United States Patent [19]

Wlodarczyk et al.

[11] Patent Number: 4,924,870

[45] Date of Patent: May 15, 1990

[54] FIBER OPTIC SENSORS

[75] Inventors: Marek T. Wlodarczyk, Birmingham; Luciano Coletta, Ypsilanti; James A. Campbell, Ann Arbor; Douglas G. Tomasko, Ypsilanti, all of Mich.

[73] Assignee: Fiberoptic Sensor Technologies, Inc., Ann Arbor, Mich.

[21] Appl. No.: 297,069

[22] Filed: Jan. 13, 1989

[51] Int. Cl.$^5$ ................................ A61B 5/02
[52] U.S. Cl. ................................ 128/667; 128/675; 128/748; 73/705
[58] Field of Search ................ 128/664–667, 128/672–673, 675, 748, 633–634; 73/705, 708, 715

[56] References Cited

U.S. PATENT DOCUMENTS

| | | | |
|---|---|---|---|
| 4,588,294 | 5/1986 | Siegmund | 128/634 X |
| 4,593,701 | 6/1986 | Kobayashi et al. | 128/667 |
| 4,691,709 | 9/1987 | Cohen | 128/667 |
| 4,703,757 | 11/1987 | Cohen | 128/667 |
| 4,711,246 | 12/1987 | Alderson | 128/748 X |
| 4,730,622 | 3/1988 | Cohen | 128/667 |
| 4,787,396 | 11/1988 | Pidorenko | 128/748 X |

*Primary Examiner*—Angela D. Sykes
*Attorney, Agent, or Firm*—Harness, Dickey & Pierce

[57] ABSTRACT

Serveral improvements in fiber optic sensing systems are disclosed. One improvement incorporates a dielectric filter applied directly to the sensing end of an optical fiber detector which has the characteristic that it reflects back a reference light beam of one wavelength while passing a sensing signal of a different wavelength which is modulated in some predetermined fashion beyond the filter. Both light signals are reflected back through the fiber and are, accordingly, attenuated in the identical or nearly identical fashion in response to various noise sources. The ratio of the intensity of the two signals is proportional to the sensed parameter and renders the system essentially self-compensating. The dielectric filter is preferably directly coated onto the exit end of the fiber through vapor deposition techniques. Time division multiplexing is used to sequentially fire plural light sources and a single photodetector is used for measuring the intensity of the reflected back signals of the various wavelengths. Another improvement encompasses the detection unit in which the input and reflected signals are separated using an off-axis parabolic mirror which provides excellent separation efficiency. According to another principal feature of this invention, a concave surface is formed at the fiber end which increases the numerical aperture of the fiber which provides greater sensitivity to the deflection of a pressure sensitive diaphragm spaced from the confronting the fiber end.

18 Claims, 5 Drawing Sheets

FIBER OPTIC SENSORS

BACKGROUND OF THE INVENTION

The present invention is related to a fiber optic sensing system and particularly to one enabling an environmental parameter to be sensed using a miniaturized sensing tip at one end of an optical fiber.

Optical fiber sensing systems can be used for a variety of applications. For example, the measurement of intravascular blood pressure of human patients has been accomplished using equipment manufactured by applicants in which a diaphragm at the fiber sensing tip deforms in response to a pressure differential and modulates light sent through the fiber in accordance with its deflection. Changes in the distance between the deformable diaphragm and the optical fiber tip changes the amplitude of light that is reflected back into the optical fiber. Accordingly, the intensity of the returned light is related to the sensed pressure. Numerous other applications for such systems exist, such as for measuring pressure of other fluids, measurement of temperature, index of refraction, etc.

Although applicants have had excellent success in implementing fiber optic sensors of the above type for intravascular blood pressure measurement, additional refinements for such system are being strived for. In medical applications, it is preferred to employ a disposable optical fiber with a sensing tip which is used as a catheter. To minimize the expense of using such a system, it should accommodate the use of relatively inexpensive plastic or glass optical fiber materials while providing acceptable accuracy and sensitivity. In order to enable the use of such low cost fibers, the system must accept a large degree of fiber-to-fiber variability in index of refraction and attentuation, and fiber bending sensitivity.

In applicants' previously designed system as described in issued U.S. Pat. No. 4,711,246 which is hereby incorporated by reference, the catheter is placed in position and a precisely controlled pressure signal is applied through the fiber to one side of the diaphragm, which produces deflection of the diaphragm. The intensity of the returned light is evaluated and used for calibration of the system. Thereafter, the measured intensity signal is compared to a software look-up table to generate an output indicating pressure at the sensing tip of the catheter.

Although the previously described calibration approach is capable of eliminating or reducing the effects of many sources of measurement inaccuracy, many contributions to inaccuracy are not addressed. Optical fibers in general, and particularly low cost plastic and glass fibers, exhibit a substantial change in light attenuation dependent upon their bending radius. In intravascular blood pressure measurement, even after the calibration steps, dynamic bending can occur due to pressure pulses or movement of the fiber inside or outside of the patient. In addition, certain optical fiber couplers exhibit changes in their characteristics due to mechanical inputs during use. Other sources of measurement inaccuracy or noise are the time dependent characteristics of the light sources and photodetectors (i.e., changes in intensity or sensitivity) which are used with such a measurement system. Due to these time dependent factors, it is present operating procedure with current amplitude based fiber optic systems to allow the electronics to reach a steady state operating temperature before use, which may require one hour or more. Such warm-up time requirements can be intolerable in some conditions such as for emergency surgery.

In view of the foregoing, it is an object of the present invention to provide a fiber optic sensing system which is essentially self-compensating in nature to reduce the effects of measurement noise generated by the previously mentioned factors.

In addition to the need to reduce measurement noise, designers of optical fiber sensing systems using deflectable diaphragms are further striving to enhance the sensitivity of such devices by increasing the changes in returned light intensity in response to deflection of the diaphragm. Accordingly, it is another object of the present invention to provide an optical fiber sensing system which provides enhanced measurement sensitivity.

For fiber optic sensors of the type described previously in which an input light signal is transmitted through the fiber and returned after being modulated in some manner, it is necessary to inject the input light signal into one end of the optical fiber and evaluate the returned signal at the same end of the fiber. Typically, beam splitters in the form of planar partially reflective mirrors are used for this purpose. Such beam splitter systems, however, are inefficient in terms of coupling the full output of the light source into the fiber and further do not provide a high degree of isolation of the returned signal from the input signal at the photodetector.

It is therefore another principal object of the present invention to provide a beam separator for a fiber optic sensing system which enhances the isolation of the returned light signal from the input light signal.

SUMMARY OF THE INVENTION

In accordance with a principal feature of the present invention, a fiber optic sensing system is provided with a wavelength referencing feature which reduces measurement noise induced by bending sensitivity of the fibers, coupler changes, and thermal effects influencing the system. The system incorporates a wavelength selective dielectric filter which is coated onto the sensing end of the optical fiber. The filter reflects back a reference or calibration optical signal while transmitting a sensing signal of a differing wavelength which is modulated in response to an environmental parameter and then reflected back into the fiber. At the sensing end, the two signals are separated and their intensity is measured. The ratio of the intensity of the two signals is used to provide a measure of the parameter being detected. Since both signals traverse the entire optical length of the fiber and are perturbed in a similar manner by bending attenuation, couplers, etc., the ratio between these two signals generates the appropriate output signal in response to the measuring modulation mechanism, essentially unaffected by such noise sources. Moreover, since it can be assumed that light sources which produce the reference and sensing light beams behave similarly, changes in their output power with respect to time will be uniform and will also be self-correcting through the ratio measurement. If desired, however, a closed loop intensity control system can be used to equalize the light source outputs or compensate in some other manner for source intensity variations.

A fiber optic measuring system which generally provides the previously mentioned features is described by U.S. Pat. No. 4,356,396. Although systems for wavelength reference of a fiber optic sensing devices as exemplified by the above patent are known generally, such prior art devices have several significant drawbacks. The dielectric filter according to the prior art patent is a separate component which must be fabricated and attached to the sensing end of the fiber. This requirement would almost necessarily render the sensing tip more bulky than one without this feature. In accordance with this invention, a dielectric wavelength selective filter is directly coated onto the fiber end through vapor deposition or other suitable techniques. Such a process enables a large number of fibers to be treated simultaneously and would not appreciably increase the size of the sensing tip.

Another shortcoming of the prior art fiber optic sensing systems employing wavelength referencing described by the above patent is the fact that both light sources are operated simultaneously to generate a combined input signal which is fed through the optical fiber. The returned signal includes both wavelengths which must be separated using a beam splitter and filters to provide signals for two discrete photodetectors. The requirement of a beam splitter reduces the intensity of the returned signal at the photodetector and, combined with the necessity of using wavelength selective filters, produces a low intensity signal incident on the photodetector. Such a system is also vulnerable to changes in characteristics of each of the photodetectors during operation which is a source of measurement noise which is not compensated for by the dual wavelength referencing system of the prior art.

In accordance with the present invention, time division multiplexing is used such that the differing wavelength light sources are operated alternately. A single photodetector is used which is sensitive to both wavelengths and a synchronization signal is used to separate outputs generated by the two light sources. This approach reduces the complexity of the measurement system and renders it insensitive to additional sources of noise.

In accordance with another principal feature of this invention, the numerical aperture of the fiber is increased through the formation of a concave surface at the optical fiber sensing tip end. Such a concave surface increases the cone angle of light emitted from the fiber (and the reception angle) which produces a greater change in returned light signal intensity in response to movement of the deformable membrane. Accordingly, the provision of such a concave surface enhances the sensitivity of the system.

Applicants were recently granted U.S. Pat. No. 4,787,396, which relates to an improved fiber optic sensor in which a convex lens surface is formed at the sensing tip end of the fiber. For this system, the deformable membrane is positioned beyond the focal point of the lens. This approach enhanced the measurement sensitivity of the system, but has several features which are disadvantages in some applications. The spacing of the membrane from the fiber end becomes very critical for such systems. Moreover, the increased distance of the reflective membrane surface from the terminal end of the fiber reduces the intensity of returned light. It has further been found that the convex lens approach is quite sensitive to asymmetry and inclination of the axis of generation of the lens. The concave lens approach is believed to be less sensitive to minor imperfections in lens shape and can operate with the membrane extremely close to the fiber end.

Another feature of this invention is the provision of a beam separator which injects the input beam into the fiber and receives and focuses the returned light onto a photodetector. The separator employs an off-axis parabolic mirror with a central aperture through which the input beam passes. The returned beam is defocused to a large diameter which strikes the mirror and is focused onto the detector. This system provides excellent separation of the returned signal from the input signal.

Although the previously mentioned improvements for fiber optic sensing systems can be incorporated in a single device, they can also be implemented separately. The wavelength referencing approach can be used with fibers having variously shaped terminal ends (i.e., concave, flat, convex) for providing enhanced accuracy and resistance to measurement noise and can be used with various beam separators. Similarly, the concave fiber end surface can be implemented with a bare fiber or one having a dielectric interference filter coating as a means of enhancing numerical aperture and therefore measurement sensitivity. The beam splitter arrangement may likewise be used separately from the previously mentioned concepts and can be implemented in fiber optic sensors in which the returned signal is modulated in manners besides amplitude.

Additional benefits and advantages of the present invention will become apparent to those skilled in the art to which this invention relates from the subsequent description of the preferred embodiments and the appended claims, taken in conjuction with the accompanying drawings.

DETAILED DESCRIPTION OF THE INVENTION

Figure 1:
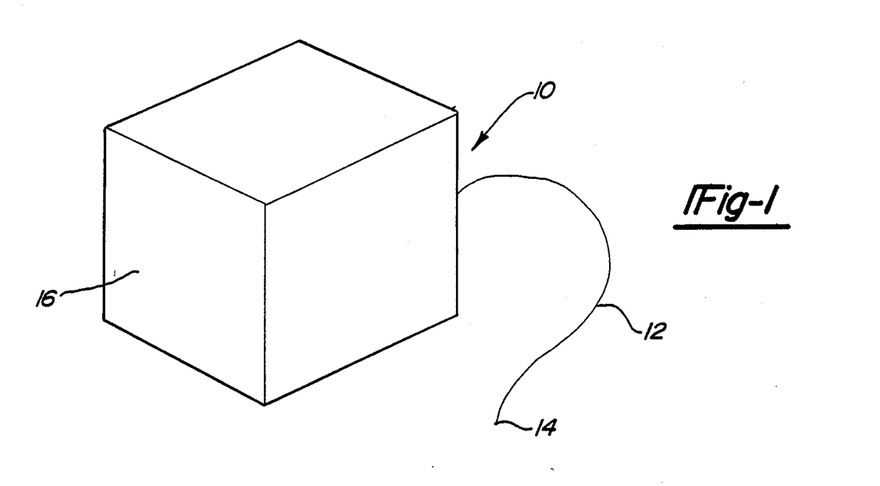
FIG. 1 is a pictorial view of a fiber optic sensing system in accordance with this invention particularly adapted for measurement of intravascular blood pressure.

FIG. 1 provides a pictorial view of a fiber optic sensing system in accordance with this invention which is generally designated by reference number 10. System 10 incorporates an elongated optical fiber 12 with a sensing tip 14 which modulates an input light signal to measure an environmental parameter such as fluid pressure. Detection unit 16 houses the electronic and optical elements of the system. For use for intravascular blood pressure measurement, optical fiber 12 and sensing end 14 would be disposable (i.e., single use) units.

Figures 2, 3:
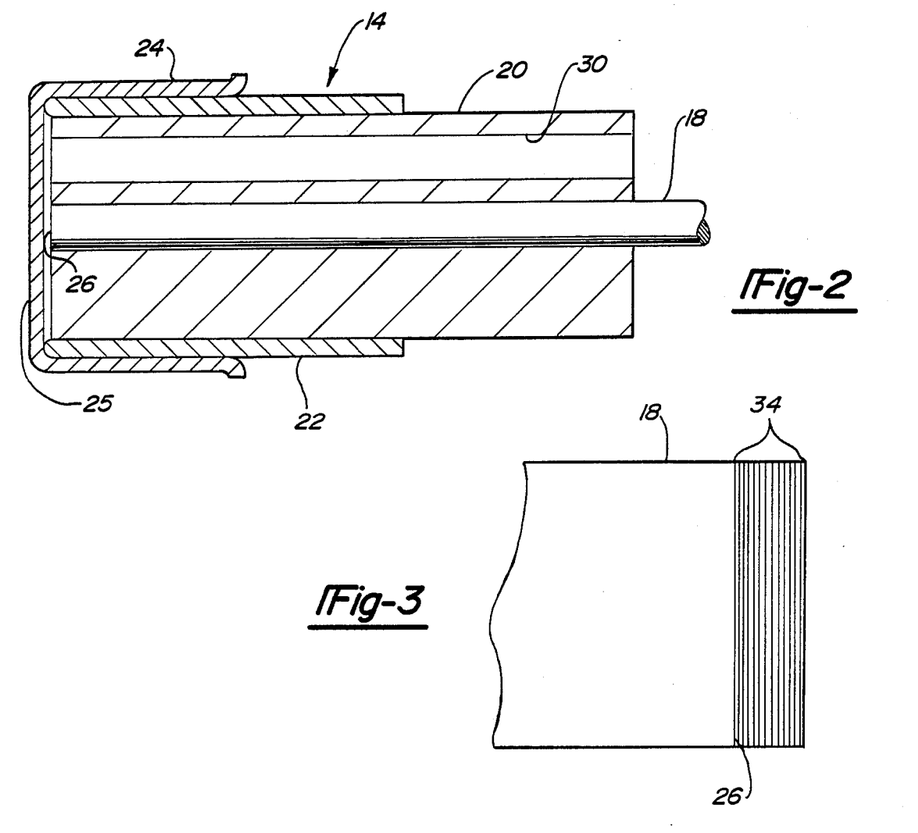
FIG. 2 is an enlarged longitudinal cross-sectional view of a sensing tip for an optical fiber sensing system in accordance with the present invention.
FIG. 3 is an enlarged cutaway cross-sectional view taken from FIG. 2 illustrating multiple layers of dielectric material applied to the end surface of the optical filament which acts as a light wavelength selective filter.

FIG. 2 is a cross-sectional view of sensing tip end 14 of optical fiber 12. As shown, a single optical filament 18 passes through ferrule 20 to which it is bonded or interference fit. Cylinder 22 surrounds ferrule 20. Diaphragm cap 24 is placed over cylinder 22 and has a center membrane portion 25 which deforms in response to variations in differential pressure across it. Input light is sent through filament 18 and strikes the center area of membrane 25 and is reflected back into the fiber. A casing (not shown) encases and protects filament 18 and is connected to detection unit 16. The intensity of returned light is modulated by the separation between and fiber end surface 26. Detection unit 16 provides the input light beam membrane 25, measures the intensity of the returned back signal and compares the intensity to an internal calibration table to output a pressure value. A vacuum signal of a known level can be applied to the inside surface of diaphragm cap 24 through the casing and vent passage 30 for calibration purposes.

FIG. 3 provides an enlarged view of the end surface 26 of filament 18 which incorporates a wavelength selective dielectric filter 34, showing the thickness of layers comprising the filter greatly enlarged for illustration. Filter 34 is formed by depositing multiple layers of thin films of material of different indexes of refraction and specific thicknesses. In a preferred embodiment, dielectric filter 34 comprises numerous layers, for example twenty layers, of titanium dioxide and silicone dioxide with the material alternating between layers. The layers comprising filter 34 are directly coated onto the filament ends by vapor deposition or other suitable processes. The presence of filter 34 does not complicate the process of assembling tip 14 or render it more bulky due to the minute thickness of the film.

Figure 4:
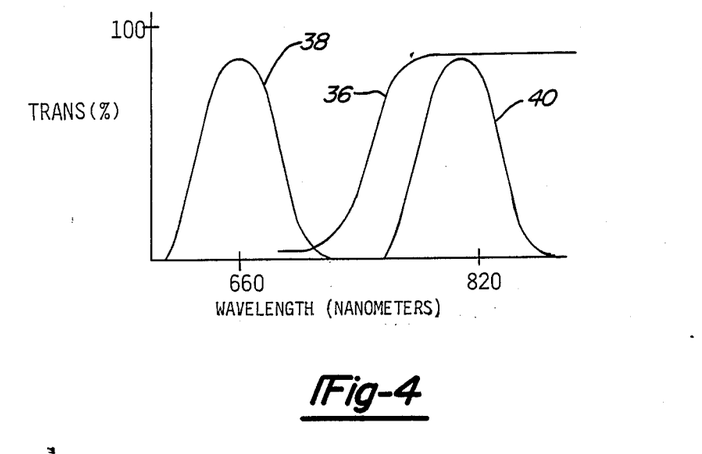
FIG. 4 is a transmission versus wavelength spectrum for a pair of light sources used in the system according to this invention and showing the transmission characteristic of the interference filter shown in FIG. 2.

The spectral characteristics of filter 34 are graphically illustrated in FIG. 4. Curve 36 illustrates that dielectric filter 34 provides a long wavelength pass characteristic with longer light being reflected back through filament 18. Longer wavelength light passes through filter 34 without significant attenuation. FIG. 4 also illustrates the output spectra of a pair of light sources which may be used in implementing this invention. Curve 38 is a light source such as an LED which emits light of a wavelength, for example, of 660 nanometers which would be reflected back by dielectric filter 34 and acts as a reference or calibration signal. The sensing light signal which may also be generated by an LED is represented by curve 40 and has a central output at about 820 nanometers which passes through dielectric filter 34. Light sources 42 and 44 have output spectra within transmission windows of a plastic optical fiber material (i.e., spectral regions where transmission is high). As previously explained, the reference signal is reflected by dielectric filter 34 and is attenuated by the same sources of attenuation as the sensing signal. Differences in attenuation between the reference and sensing signals are caused by diaphragm position which affects only the sensing signal. By comparing the ratio of these two intensity levels of the returned signal, the modulated components of the sensing signal can be separated from noise sources. The modulation and noise source of both the reference and sensing signals can be characterized as exponential:

$$S = s \exp[-n(t)] \quad R = r \exp[-n(t) - x(t)]$$

where
s = sensing signal strength
r = reference signal strength
n = noise
x = diaphragm displacement then the log ratio can be used to produce a noise-cancelled output:

$$x(t) = \log S/R$$

Figure 5:
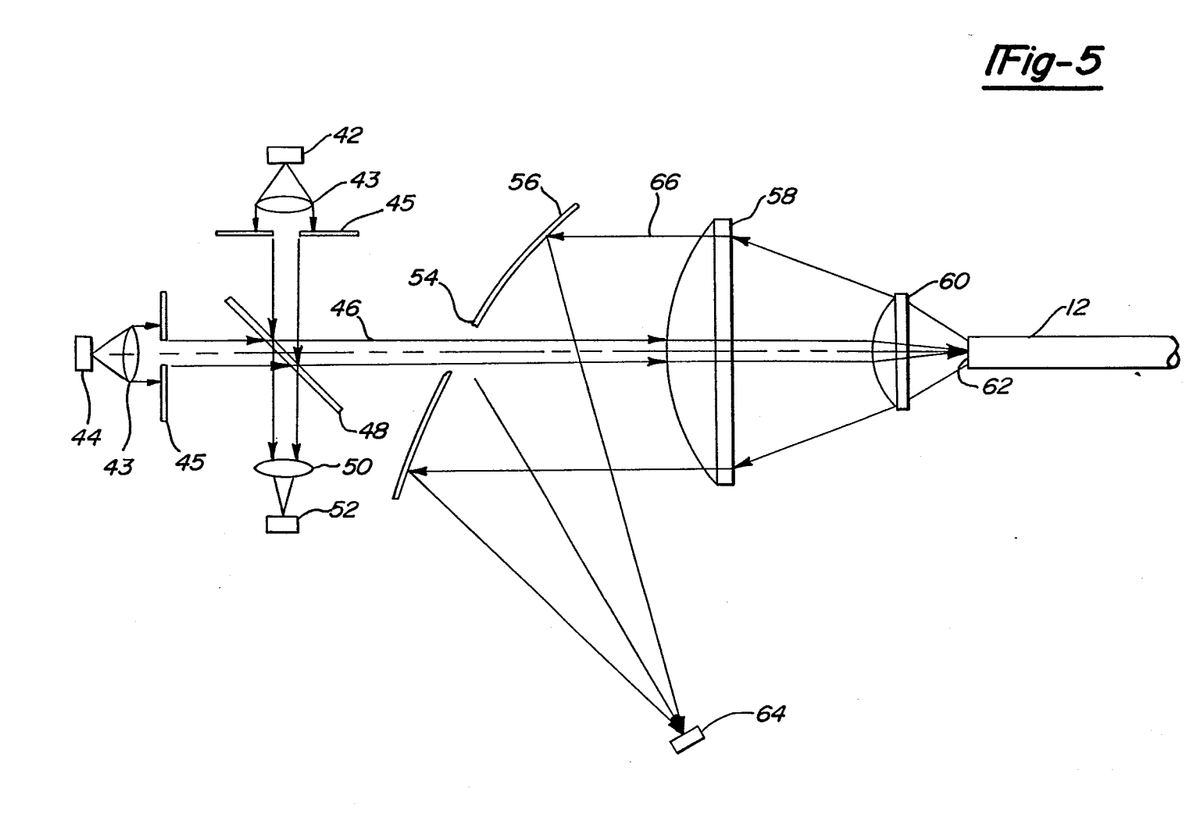
FIG. 5 is a diagrammatic illustration of a beam separator in accordance with this invention incorporating an off-axis parabolic mirror.
Figure 6:
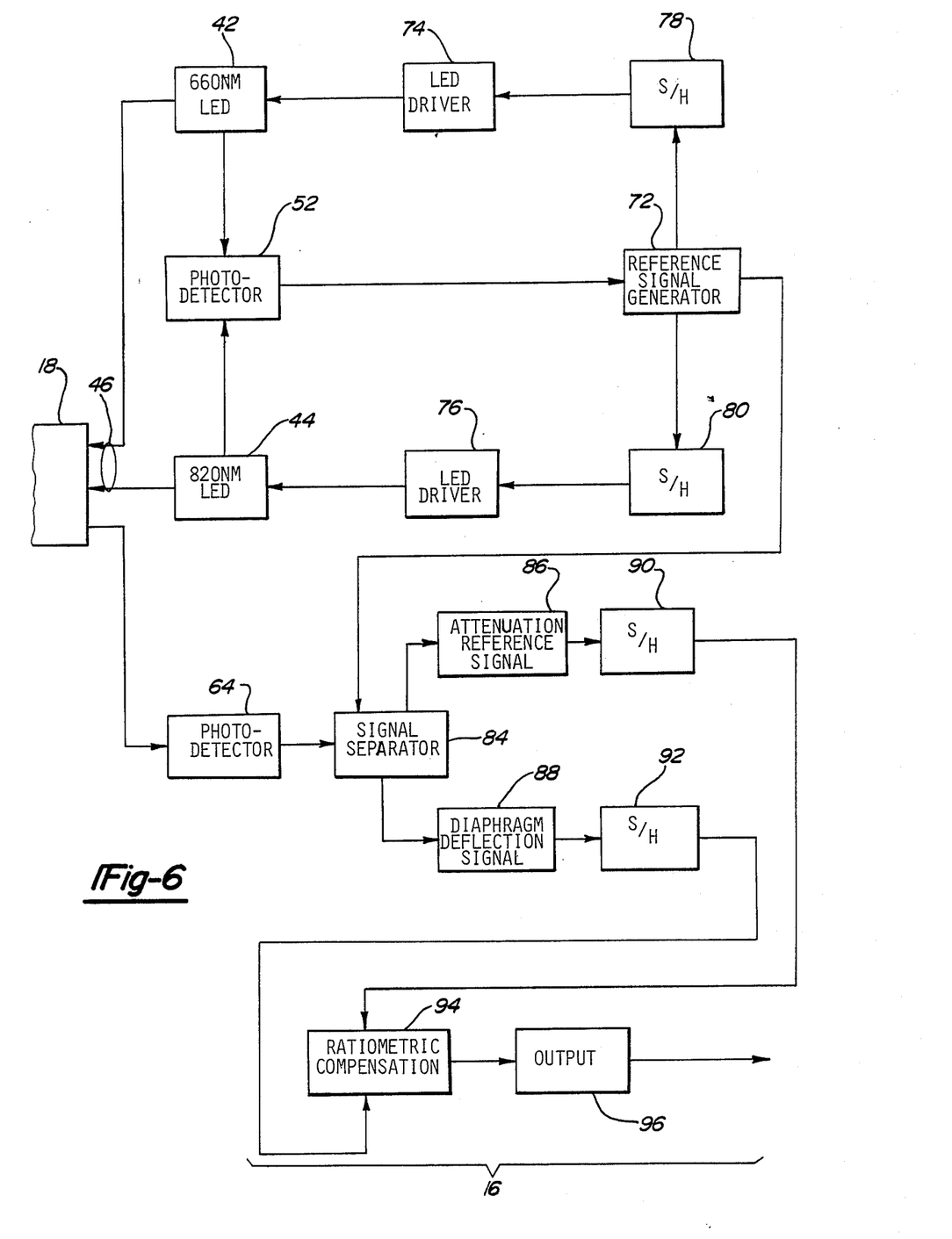
FIG. 6 is a schematic diagram of the electronic and optical elements of the detector unit of the optical fiber sensing system according to this invention which provides time division multiplexing for the reference and sensing light signals.

Now with reference to FIGS. 5 and 6, the optical and electronic components of detection unit 16 are shown. As shown in FIG. 5 which illustrates a beam separator 68 in accordance with an aspect of this invention, a pair of LED light sources 42 and 44 are used to provide the relatively lower frequency reference signal (e.g., 660 nanometers) and the relatively shorter wavelength sensing signal (e.g., 820 nanometers), respectively. Lenses 43 collimate the beams and apertures 45 limit beam diameter. Light outputted from LEDs 42 and 44 are combined into a coaxial input beam 46 by planar beam splitter 48. Beam splitter 48 also directs a portion of the light from both LEDs 42 and 44 onto automatic intensity control photodetector 52 through focusing lens 50. Photodetector 52 can be employed to either directly modulate the current applied to LEDs 42 and 44, or could be used to measure their output intensity to provide calibration of the returned signal. Lens 43 and aperture 45 provide a narrow collimated beam 46 which passes through aperture 54 within parabolic mirror 56. The input beam 46 then passes through focusing lenses 58 and 60 where it is focused and injected into input end 62 of filament 18.

The signal that is returned along fiber 12 exits input end 62 at a dispersion or cone angle as illustrated in FIG. 5. This signal can be comprised of light from a single light source or various sources as when the previously described wavelength referencing scheme is used. Lenses 58 and 60 expand the returned beam and then collimate it such that it strikes parabolic mirror 56. The optical axis of mirror 56 is tipped from beams 46 and 66 so that the returned light beam is focused onto photodetector 64. This system provides very high optical efficiency since the input signal is applied to fiber inlet end 62 without significant attenuation. Similarly, since the reflected back beam is expanded to a much greater diameter than the input beam, the only loss in intensity of the returned beam is attributable to the relatively small cross-sectional area defined by aperture 54, thus providing excellent signal strength at photodetector 64.

In operation, LEDs 42 and 44 are alternately energized in a pulsed fashion with a dwell period between pulses. Using appropriate signal conditioning electronics as explained in general below, photodetector 64 detects the intensity of both the reference and sensing light signals and sorts the received signals through a synchronization signal from a controller to discriminate the intensity readings for both the reference and sensing signals. Photodetector 52 is employed for an intensity control system to control the current applied to LEDs 42 and 44 to provide a desired output intensity. For applications in which beam separator 68 is used in a system using a single light source, photodetector 64 would directly sense and output a signal related to returned light intensity without requiring synchronization with the source.

FIG. 6 provides a block diagram of the electronic and optical components of detection unit 16 with the beam separator 68 of FIG. 5 removed for clarity. Reference signal generator 72 provides triggering signals for the entire system and controls the time division multiplexing operation. Triggering signals are applied to reference signal LED 42 and sensing signal LED 44, respectively, through LED drivers 74 and 76. Photodetector 52 provides a signal for intensity control or calibration and receives a timing signal from generator 72 to enable it to distinguish between light from sources 42 and 44. Sample-and-hold circuits 78 and 80 provide appropriate synchronization to allow the light and dark currents to be measured from intensity control photodetector 52. In other words, the sample-and-hold circuits allow sampling of photodetector current after a light pulse is received and before the next pulse arrives.

The signals that are returned along filament 18 are sensed by photodetector 64. Signal separator 84 is a switching network synchronized by reference signal generator 72 to permit separation of the returned beam 66 from LED sources 42 and 44 from each other. Accordingly, returned light from reference LED 42 produces an attenuation reference signal 86, and returned light from sensing LED 44 produces diaphragm deflection signal 88. Sample-and-hold circuits 90 and 92 are employed to provide a memory or time delay so that the intensities of these signals can be directly compared at the same time by radiometric compensator or comparator 94 and measures dark current in the same way as photodetector 52. Comparator 94 provides an output 96 which is fed through appropriate signal processing electronics, for example, as described by applicants' previously issued U.S. Pat. No. 4,711,246 to provide an output of the parameter being measured.

Figure 7:
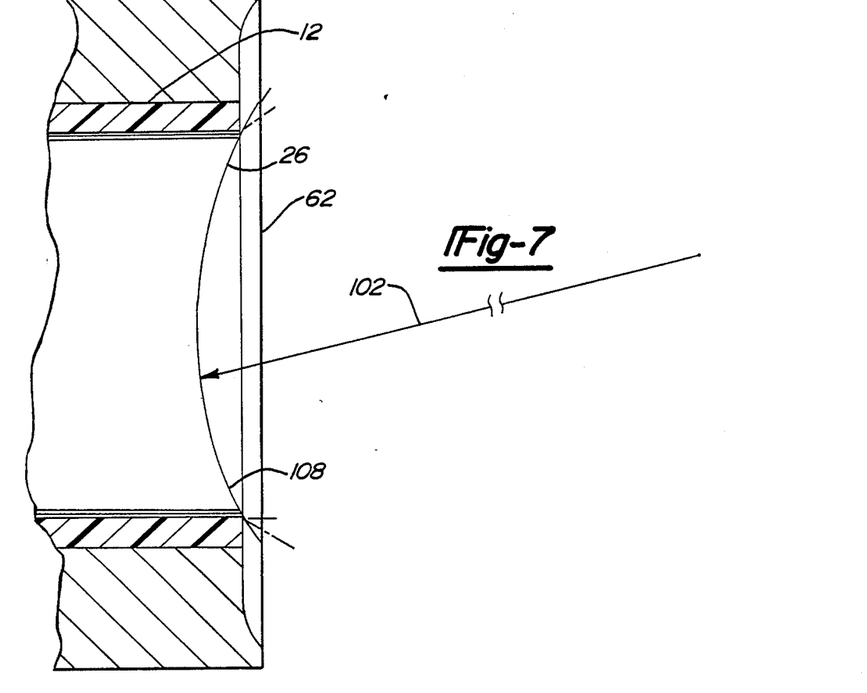
FIG. 7 is an enlarged cross-sectional view similar to FIG. 1 except showing another feature of the present invention in which the end of the optical filament is formed to a concave configuration.
Figure 8:
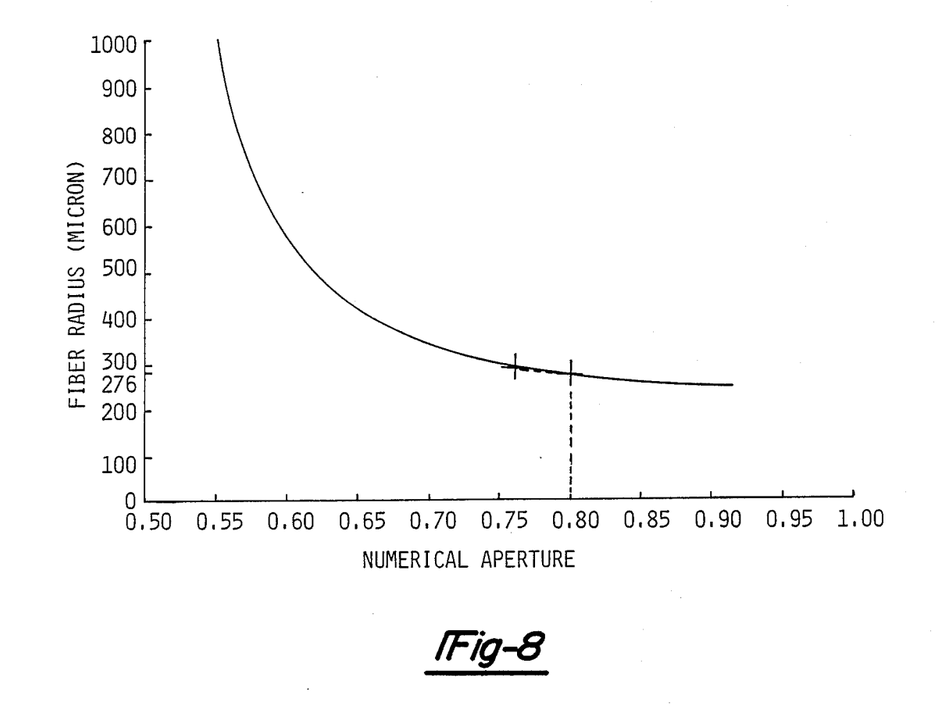
FIG. 8 is a graph illustrating the relationship between the radius of curvature of the concave end of an optical filament versus the numerical aperture of the fiber.
Figure 9:
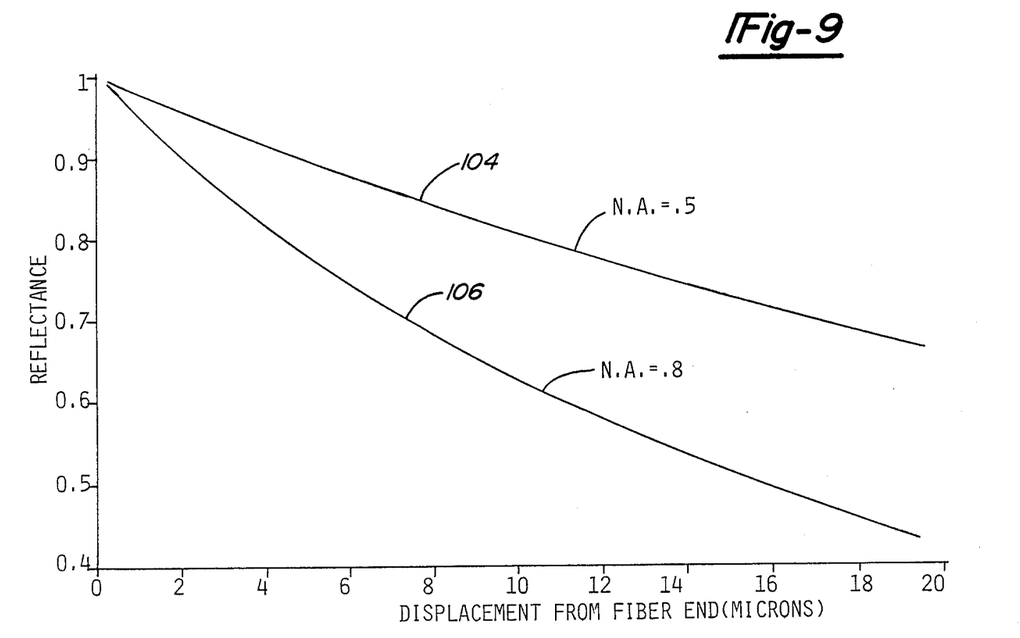
FIG. 9 illustrates the relationship of returned light intensity versus the diaphragm's distance from an optical fiber core end for fibers having differing numerical apertures.

With reference to FIG. 7, another principal feature of the present invention is illustrated which enhances sensitivity of the system. As shown, end 26 of filament 18 is formed with a concave surface 108. As illustrated, the concave surface is hemispherical in shape and has a radius of curvature shown by radius line 102. The provision of such a concave surface increases the numerical aperture of fiber assembly 12. The relationship between the radius of curvature of concave end 108 and the resulting numerical aperture is illustrated in FIG. 8. As shown, substantial increases in numerical aperture are provided, particularly when the radius of curvature is below about 300 microns. In one experimental embodiment of the present invention, a radius of curvature of 276 microns was used which provided a 0.8 numerical aperture. Enhancements in numerical aperture increase the cone angle of light emitted from (and received by) fiber end 26. This characteristic has been shown to increase the sensitivity of the system to changes in deflection or distance of diaphragm membrane 25 from the fiber end. This characteristic is illustrated graphically by FIG. 9. Curve 104 illustrates the relationship between diaphragm displacement and reflectance for a fiber having a relatively low numerical aperture of 0.5, for example. Curve 106 shows this relationship for a fiber having a 0.8 numerical aperture. The slopes of curves 104 and 106 determine the sensitivity of the system. While the slopes of the curves tend to become nearly equal to one another beyond a displacement distance of about ten microns, there is a significant enhancement of slope between zero and ten microns for the high numerical aperture fiber. Accordingly, fibers having concave ends in accordance with this invention would preferably be operated in such a range of high sensitivity. Concave end surface 108 can be formed by machining processes and perhaps also by direct molding or heat melting. Moreover, the concave surface could also be formed by a separate lens which would be bonded to fiber end 26.

While the above description constitutes the preferred embodiments of the present invention, it will be appreciated that the invention is susceptible of modification, variation and change without departing from the proper scope and fair meaning of the accompanying claims.

We claim:

1. A fiber optic sensing system comprising:
   an optical fiber having first and second terminal ends,
   first light emitting means for producing an input reference light signal,
   second light emitting means for producing an input sensing light signal of a wavelength different from that produced by said first light emitting means,
   optical means for inputting said reference and sensing light signals into said first fiber end,
   a sensing tip fastened to said fiber second end and having measuring means for modulating said sensing light signal in response to a parameter to be measured,
   a wavelength selective filter adjacent said second terminal end which allows said sensing light signal passing through said filter to be modulated by said measuring means while returning said reference signal,
   photodetector means for sensing the intensity of said reference and sensing light signals returned through said second fiber end, and
   controller and signal processing means for controlling said first and second light emitting means to produce alternate pulses of light from each of said light emitting means and for processing signals from said photodetector means to separate said returned reference light signal from said returned sensing light signal, and for comparing the intensity of said returned reference and sensing signals to provide an output related to said parameter to be measured.

2. A fiber optic sensing system as set forth in claim 1 wherein said measuring means comprises a diaphragm overlying said fiber second end which deforms in response to pressure differentials and varies the intensity of said returned sensing light signal returned into said fiber dependent on its spacing from said fiber second end.

3. A fiber optic sensing system as set forth in claim 1 wherein said wavelength selective fiber is a dielectric filter applied onto said fiber second end.

4. A fiber optic sensing system as set forth in claim 1 wherein said reference signal is of a shorter wavelength than said sensing signal.

5. A fiber optic sensing system as set forth in claim 1 wherein said wavelength selective filter comprises alternate layers of silicon dioxide and titanium dioxide directly coated onto said fiber second end.

6. A fiber optic sensing system as set forth in claim 1 wherein said controller and signal processing means is further for measuring the intensity of light outputted by said first and second light emitting means before said light signals are injected into said fiber for controlling the output of said first and second light emitting means.

7. A fiber optic sensing system as set forth in claim 1 wherein said photodetector means comprises a single photodetector element which receives both said returned reference and sensing light signals.

8. A fiber optic sensing system comprising:
an optical fiber having first and second terminal ends,
a wavelength selective filter adjacent said second terminal end including numerous layers of dielectric materials directly deposited onto said fiber second end having the characteristic that said filter transmits light within a first range of wavelength and reflects light within a second range of wavelengths,
first light emitting means for producing a reference light signal within said second range of wavelengths,
second light emitting means for producing a sensing light signal of a wavelength different than that produced by said first light emitting means and within said first range of wavelengths,
optical means for injecting said reference and sensing light signals into said first fiber end,
a sensing tip fastened to said fiber second end and having measuring means for modulating said sensing light signal in response to a parameter to be measured,
photodetector means for sensing the intensity of said reference and sensing light signals returned through said fiber, and
controller and signal processing means for evaluating the intensity of said returned reference and sensing light signals and providing an output related to said parameter to be measured.

9. A fiber optic sensing system as set forth in claim 8 wherein said controller and signal processing means further comprises means for controlling said first and second light emitting means to produce alternate pulses of light and for processing signals from said photodetector means to separate signals related to said returned reference light signal from signals related to said returned sensing light signal, and for comparing the intensity of said returned reference and sensing signals to provide an output related to said parameter to be measured.

10. A fiber optic sensing system as set forth in claim 8 wherein said reference signal is of a lower wavelength than said sensing signal and is reflected back by said filter.

11. A fiber optic sensing system as set forth in claim 8 wherein said controller and signal processing means is further for measuring the intensity of light outputted by said first and second light emitting means before said light signals are injected into said fiber for controlling the output of said first and second light emitting means.

12. A fiber optic sensing system as set forth in claim 8 wherein said measuring means comprises a diaphragm overlying said fiber second end which deforms in response to pressure differentials and varies the intensity of said returned sensing light signal dependent on its spacing from said fiber second end.

13. A beam separator assembly for a fiber optic sensing system of the type having a sensing tip with measuring means for sensing a parameter to be measured and modulating the intensity of a sensing light signal which is returned back through an optical fiber, comprising:
light source means for generating a sensing light signal,
first optical means for inputting said sensing light signal into an end of said optical fiber,
a parabolic mirror having an aperture through which said sensing light signal passes before being injected into optical fiber,
second optical means for enlarging the returned light signal exiting said optical fiber end and directing said returned signal onto said parabolic mirror around said aperture, said parabolic mirror having an optical axis tipped from that of said input and returned sensing light signal, and
photodetector means for receiving and measuring the intensity of light focused by said parabolic mirror.

14. A beam separator assembly as set forth in claim 13 wherein said light source means includes at least two discrete light sources generating light of different wavelengths and wherein the light from said two sources is combined coaxially by a beam splitter to define said input beam.

15. A beam separator assembly for a fiber optic sensing system of the type having a sensing tip with measuring means for sensing a parameter to be measured and modulating the intensity of a sensing light signal which is returned back through an optical fiber, comprising:
light source means for generating a sensing light signal,
first optical means for inputting said sensing light signal into an end of said optical fiber along an optical axis,
second optical means for receiving said returned signal emitted from said fiber end along said optical axis and for expanding said returned beam to a diameter larger than said input light beam,
a parabolic mirror positioned along said optical axis for receiving and focusing said returned light beam, said mirror having an optical axis inclined from said beam optical axis, and
photodetector means for receiving and measuring the intensity of light focused by said parabolic mirror.

16. A beam separator as set forth in claim 15 wherein said input beam passes through an aperture within said mirror.

17. A fiber optic sensing system comprising:
an optical fiber having first and second terminal ends,
a wavelength selective filter adjacent said second terminal end including numerous layers of dielectric materials directly deposited onto said fiber second end having the characteristic that said filter transmits light within a first range of wavelength and reflects light within a second range of wavelengths,
first light emitting means for producing a reference light signal within said second range of wavelengths,
second light emitting means for producing a sensing light signal of a wavelength different than that produced by said first light emitting means and within said first range of wavelengths, optical means for injecting said reference and sensing light signals into said first fiber end, a sensing tip fastened to said fiber second end and having measuring means for modulating said sensing light signal in response to a parameter to be measured, photodetector means for sensing the intensity of said reference and sensing light signals returned through said fiber, and controller and signal processing means for evaluating the intensity of said returned reference and sensing light signals and providing an output related to said parameter to be measured, and further having means for controlling said first and second light emitting means to produce alternate pulses of light and for processing signals from said photodetector means to separate signals related to said returned reference light signal from signals related to said returned sensing light signal, and for comparing the intensity of said returned reference and sensing signals to provide an output related to said parameter to be measured.

18. A fiber optic sensing system comprising:

an optical fiber having first and second terminal ends, a wavelength selective filter adjacent said second terminal end including numerous layers of dielectric materials directly deposited onto said fiber second end having the characteristic that said filter transmits light within a first range of wavelength and reflects light within a second range of wavelengths, first light emitting means for producing a reference light signal within said second range of wavelengths, second light emitting means for producing a sensing light signal of a wavelength different than that produced by said first light emitting means and within said first range of wavelengths, optical means for injecting said reference and sensing light signals into said first fiber end, a sensing tip fastened to said fiber second end and having measuring means for modulating said sensing light signal in response to a parameter to be measured, photodetector means for sensing the intensity of said reference and sensing light signals returned through said fiber, and controller and signal processing means for evaluating the intensity of said returned reference and sensing light signals and providing an output related to said parameter to be measured, and further for measuring the intensity of light outputted by said first and second light emitting means before said light signals are injected into said fiber for controlling the output of said first and second light emitting means.

* * * * *